US012653395B2

(12) United States Patent
    Hara

(10) Patent No.: US 12,653,395 B2
(45) Date of Patent: Jun. 16, 2026

(54) OPHTHALMIC DEVICE

(71) Applicant: KOWA COMPANY, LTD., Nagoya (JP)

(72) Inventor: Takuya Hara, Tokyo (JP)

(73) Assignee: KOWA COMPANY, LTD., Nagoya (JP)

( * ) Notice: Subject to any disclaimer, the term of this patent is extended or adjusted under 35 U.S.C. 154(b) by 334 days.

(21) Appl. No.: 18/280,313

(22) PCT Filed: Mar. 10, 2022

(86) PCT No.: PCT/JP2022/010461
    § 371 (c)(1),
    (2) Date: Sep. 5, 2023

(87) PCT Pub. No.: WO2022/191263
    PCT Pub. Date: Sep. 15, 2022

(65) Prior Publication Data
    US 2024/0306906 A1     Sep. 19, 2024

(30) Foreign Application Priority Data

Mar. 11, 2021     (JP) ................................. 2021-039562

(51) Int. Cl.
    *A61B 3/00*          (2006.01)
    *A61B 3/12*          (2006.01)
(52) U.S. Cl.
    CPC .............. *A61B 3/0075* (2013.01); *A61B 3/12* (2013.01)
(58) Field of Classification Search
    CPC ......... A61B 3/0075; A61B 3/152; A61B 3/18; A61B 3/135; A61B 3/13; A61B 3/12; A61B 3/10; A61B 3/0091
    (Continued)

(56) References Cited

U.S. PATENT DOCUMENTS 5,412,442 A  *  5/1995  Katsuragi ................ A61B 3/14
                                                            396/18
    2013/0148082 A1*  6/2013  Hara .................... A61B 3/0091
                                                            351/221
                        (Continued)

FOREIGN PATENT DOCUMENTS

CN      112274106 A  *  1/2021  ............. A61B 3/135
    EP      2116179 A1   11/2009
                        (Continued)

OTHER PUBLICATIONS

International Search Report for PCT/JP2022/010461 dated May 24, 2022.
Japanese Office Action for 2023-505621 dated May 12, 2026.

*Primary Examiner* — Bumsuk Won
*Assistant Examiner* — Seth D Moser
(74) *Attorney, Agent, or Firm* — MOSER TABOADA

(57) ABSTRACT

An ophthalmic device (1) of the present invention has an optical head (2) including a light projection optical system (21) that projects light onto a subject eye (E), a light reception optical system (22) that receives light from the subject eye (E), and a fixation lamp (23) for guiding a line-of-sight direction of the subject eye (E), and a turning drive unit that turns the optical head (2) in a horizontal direction while maintaining positional relationships between the light projection optical system (21), the light reception optical system (22), and the fixation lamp (23). The turning drive unit is composed of a rotational drive unit (4) that rotates the optical head (2) in the horizontal direction and a horizontal drive unit (3) that moves the optical head (2) in the horizontal direction.

13 Claims, 5 Drawing Sheets

(58) Field of Classification Search
USPC ................................................. 351/206, 221
See application file for complete search history.

(56)                          References Cited

U.S. PATENT DOCUMENTS

| | | | | |
|---|---|---|---|---|
| 2013/0271727 A1* | 10/2013 | Akiba | .................... | A61B 3/152 |
| | | | | 351/205 |
| 2013/0321766 A1* | 12/2013 | Morohashi | ........... | A61B 3/1025 |
| | | | | 351/214 |
| 2015/0327763 A1* | 11/2015 | Shimizu | ................ | A61B 3/152 |
| | | | | 351/206 |
| 2015/0342452 A1* | 12/2015 | Hara | .................... | A61B 3/0025 |
| | | | | 351/224 |
| 2020/0245860 A1* | 8/2020 | Umano | ................ | A61B 3/0016 |

FOREIGN PATENT DOCUMENTS

| | | | | |
|---|---|---|---|---|
| JP | 2005-065813 A | | | 3/2005 |
| JP | 2010259495 A | | | 11/2010 |
| JP | 2011078597 A | * | | 4/2011 |
| JP | 2013-220196 A | | | 10/2013 |
| JP | 2019-047983 A | | | 3/2019 |
| JP | 2020-124347 A | | | 8/2020 |

* cited by examiner ( a )　Case of right eye

No rotation             Clockwise 15° rotation ( b )　Case of left eye

No rotation             Counterclockwise 15° rotation

OPHTHALMIC DEVICE

TECHNICAL FIELD

The present invention relates to ophthalmic devices such as a laser flare meter, a slit lamp, a fundus camera, and a scanning laser ophthalmoscope.

BACKGROUND ART

In recent years, ophthalmic devices such as a laser flare meter, a slit lamp, a fundus camera, and a scanning laser ophthalmoscope are being reduced in sizes. As the reduction in sizes of ophthalmic devices progresses, not only does the overall size of a device decrease, but also the distance between the device (its objective lens) and a subject eye, or a so-called working distance, may decrease. If the working distance decreases, the device will be positioned close to the face of a subject, so the face of the subject, especially the nose, may possibly come into contact with the device.

In this context, Patent Document 1 proposes an ophthalmic imaging device in which a chin rest for the subject to rest his/her chin includes a left-facing support for imaging the right eye and a right-facing support for imaging the left eye. According to such an ophthalmic imaging device, two supports are provided in different directions, and the support for the subject to rest his/her chin can thereby be changed in accordance with whether the subject eye is the right or left eye; therefore, the objective lens of the ophthalmic imaging device and the face of the subject can be prevented from interfering with each other.

PRIOR ART DOCUMENTS

Patent Documents

[Patent Document 1] JP2019-047983A

SUMMARY OF THE INVENTION

Problems to be Solved by the Invention

In the ophthalmic imaging device of Patent Document 1, however, the subject himself/herself has to move the body to change the support for the subject to rest the chin, which may be unfavorable because it imposes a burden on the body of the subject. In addition, when changing the support for the subject to rest the chin, there is a risk that the subject will accidentally bump the face against the device.

The present invention has been made in view of such circumstances, and an object of the present invention is to provide an ophthalmic device that can avoid contact between the device and the face of a subject without imposing a burden on the body of the subject.

Means for Solving the Problems

To achieve the above object, the present invention provides an ophthalmic device comprising: an optical head including a light projection optical system that projects light onto a subject eye, a light reception optical system that receives light from the subject eye, and a fixation lamp for guiding a line-of-sight direction of the subject eye; and a turning drive unit that turns the optical head in a horizontal direction while maintaining positional relationships between the light projection optical system, the light reception optical system, and the fixation lamp, the turning drive unit being composed of a rotational drive unit that rotates the optical head in the horizontal direction and a horizontal drive unit that moves the optical head in the horizontal direction (Invention 1).

According to the invention (Invention 1), the turning drive unit turns the optical head in the horizontal direction while maintaining the positional relationships between the light projection optical system, the light reception optical system, and the fixation lamp, so that the subject eye of the subject moves to follow the light from the fixation lamp, and the optical head can therefore be moved away from the face of the subject in a state in which the light projection optical system and the light reception optical system are still capturing the measurement site of the subject eye. This can result in an increased distance between the optical head and the face of the subject, thereby avoiding contact between the ophthalmic device and the face of the subject without imposing a burden on the body of the subject. Moreover, even in a limited space such as in a housing of the ophthalmic device, for example, the structure for turning the optical head can be achieved by appropriately arranging the rotational drive unit and the horizontal drive unit.

In the above invention (Invention 1), the turning drive unit may be preferably controlled so that the optical head turns in a direction in which a portion of the optical head suspected to come into contact with a subject moves away from the face of the subject (Invention 2).

In the above invention (Invention 2), the direction in which the portion of the optical head moves away from the face of the subject may differ between when the subject eye is the right eye and when the subject eye is the left eye (Invention 3).

In the above invention (Invention 1 to 3), the ophthalmic device may preferably further comprise: a setting unit that sets a turning angle of the optical head; and a control unit that controls the turning drive unit so as to turn the optical head in accordance with the turning angle (Invention 4).

According to the above invention (invention 4), the setting unit can set a turning angle that matches the features of the face of the subject, and the control unit can control the turning drive unit to turn in accordance with the turning angle; therefore, it is possible to achieve the turning of the optical head matching the features of the face of the subject.

In the above invention (Invention 4), the setting unit may set angle one selected from a plurality of predetermined angles as the turning angle (Invention 5), and the setting unit may set the turning angle so that the optical head turns by a predetermined unit angle (Invention 6).

In the above invention (Invention 1 to 6), the ophthalmic device may preferably further comprise a vertical drive unit that moves the optical head in a vertical direction (Invention 7).

In the above invention (Invention 7), the turning drive unit may be preferably disposed on the vertical drive unit (Invention 8).

According to the invention (Invention 8), the load applied to the turning drive unit can be reduced, and it is therefore possible to avoid an increase in the sizes of components constituting the turning drive unit.

In the above invention (Invention 8), the horizontal drive unit may be preferably disposed on the rotational drive unit (Invention 9).

According to the invention (Invention 9), since the rotational drive unit is disposed between the horizontal drive unit and the vertical drive unit, the load applied to the rotational drive unit can be reduced, and it is possible to avoid complicating the angle correction of an observation axis by the horizontal drive unit while avoiding an increase in the sizes of components constituting the rotational drive unit.

In the above invention (Invention 8, 9), the vertical drive unit may preferably include an elastic member for alleviating a load due to the rotational drive unit, the horizontal drive unit, and the optical head (Invention 10).

According to the invention (Invention 10), the presence of the elastic member can alleviate the load due to the rotational drive unit, the horizontal drive unit, and the optical head, which are arranged on the vertical drive unit, and can thus reduce the burden on the components constituting the vertical drive unit, and it is therefore possible to avoid an increase in the sizes of components constituting the vertical drive unit.

In the above invention (Invention 1 to 10), the optical head may further include a camera that images the subject eye (Invention 11).

In the above invention (Invention 11), the camera may include a front observation camera and an oblique observation camera (Invention 12).

In the above invention (Inventions 1 to 12), the light projection optical system may project projection light onto a measurement site of the subject eye obliquely with respect to an eyeball optical axis of the subject eye, and the light reception optical system may receive scattered light of the projection light that is scattered at the measurement site of the subject eye (Invention 13).

Advantageous Effect of the Invention

According to the ophthalmic device of the present invention, it is possible to avoid contact between the device and the face of a subject without imposing a burden on the body of the subject.

EMBODIMENTS FOR CARRYING OUT THE INVENTION

Figure 1:
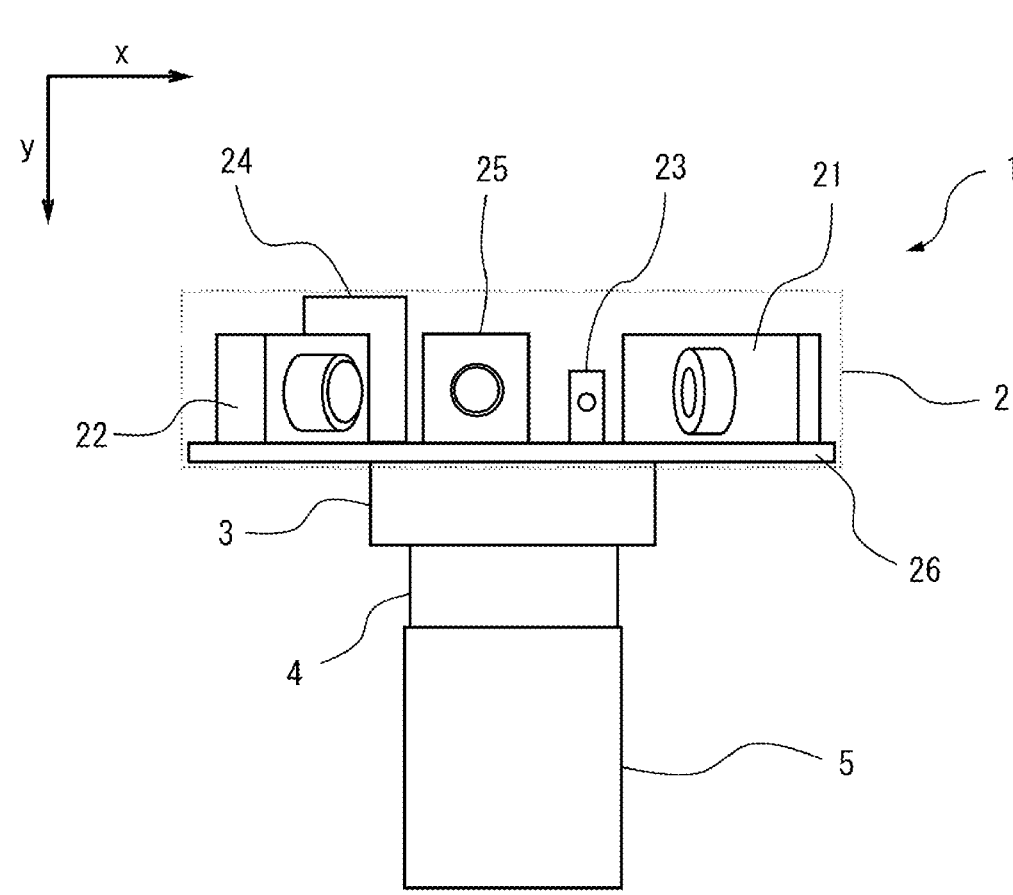
FIG. 1 is an explanatory diagram illustrating the schematic configuration of an ophthalmic device according to an embodiment of the present invention.

An embodiment of the present invention will be described with reference to the drawings. FIG. 1 is an explanatory diagram illustrating the schematic configuration of an ophthalmic device 1 according to the present embodiment, and FIG. 2 is an explanatory diagram illustrating the configuration of an optical head 2 included in the ophthalmic device 1.

The ophthalmic device 1 according to the present embodiment may be a laser flare meter as an example of ophthalmic devices. As illustrated in FIG. 1, the ophthalmic device 1 has an optical head 2, a horizontal drive unit 3 that drives the optical head 2 in the horizontal direction on a plane, a rotational drive unit 4 that rotationally drives the optical head 2 in the horizontal direction, and a vertical drive unit 5 that drives the optical head 2 up and down in the vertical direction. The horizontal drive unit 3, the rotational drive unit 4, and the vertical drive unit 5 are arranged below the optical head 2 in this order. The horizontal drive unit 3 and the rotational drive unit 4 constitute the turning drive unit of the present invention. The optical head 2, the horizontal drive unit 3, the rotational drive unit 4, and the vertical drive unit 5 may be covered with an exterior cover (not illustrated).

Figure 2:
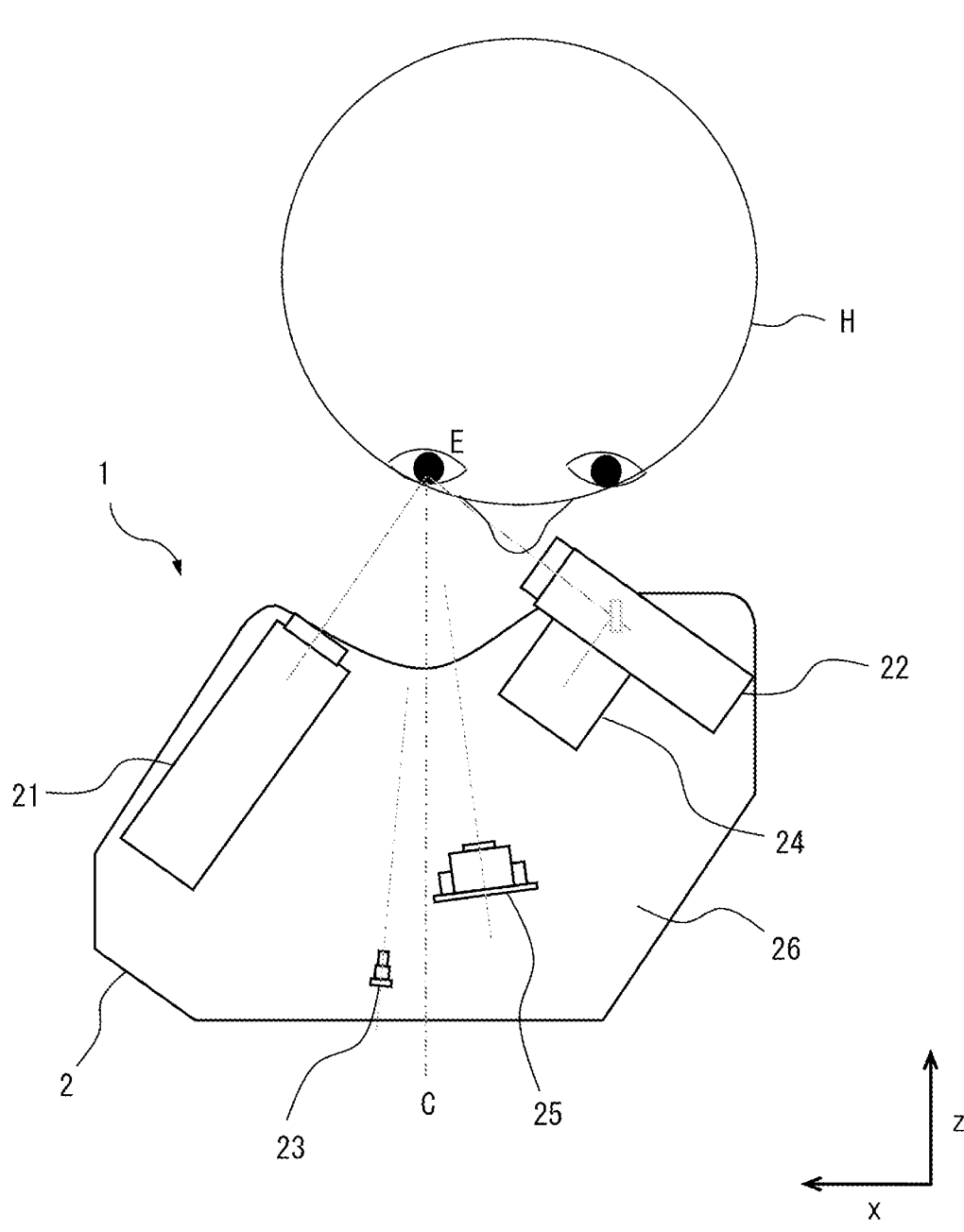
FIG. 2 is an explanatory diagram illustrating the configuration of an optical head of the ophthalmic device.

As illustrated in FIG. 2, the optical head 2 includes a light projection optical system 21 that projects light onto a subject eye E, a light reception optical system 22 that receives light from the subject eye E, a fixation lamp 23 for guiding a line-of-sight direction of the subject eye E, an oblique observation camera 24 that can observe the subject eye E from an oblique direction, and a front observation camera 25 that can observe the subject eye E approximately from the front direction.

In this specification, the term "vertical direction" is not limited to a direction that coincides with the direction of gravity, and encompasses a direction slightly inclined (e.g., about less than ±10 degrees) with respect to the direction of gravity. Likewise, the term "horizontal direction" is not limited to a direction orthogonal to the vertical direction, and encompasses a direction slightly inclined (e.g., about less than ±10 degrees) with respect to the direction orthogonal to the vertical direction. In the present embodiment, the width direction (right-left direction illustrated in FIG. 2) of the ophthalmic device 1 may be referred to as an x-axis direction, the depth direction (up-down direction illustrated in FIG. 2) of the ophthalmic device 1 may be referred to as a z-axis direction, and the height direction (up-down direction illustrated in FIG. 1) of the ophthalmic device 1 may be referred to as a y-axis direction. In FIGS. 1 and 2, the x-axis, the y-axis, and the z-axis are denoted as such. The x-axis direction and the z-axis direction each correspond to the horizontal direction, and the y-axis direction corresponds to the vertical direction.

In the optical head 2, the light projection optical system 21, the light reception optical system 22, the fixation lamp 23, the oblique observation camera 24, and the front observation camera 25 are fixed on a flat plate-shaped base 26, and the horizontal drive unit 3 and the rotational drive unit 4 are configured to be able to turn the optical head 2 in the horizontal direction while maintaining the positional relationships between the light projection optical system 21, the light reception optical system 22, the fixation lamp 23, the oblique observation camera 24, and the front observation camera 25. The ophthalmic device 1 may be a laser flare meter in the present embodiment, so the light projection optical system 21 projects projection light (laser light) onto a measurement site of the subject eye E obliquely with respect to the eyeball optical axis of the subject eye E, and the light reception optical system 22 receives scattered light of the projection light from the light projection optical system 21 that is scattered at the measurement site of the subject eye E. The illustrated shape of the base 26 and the configurations and arrangement positions of the light projection optical system 21, the light reception optical system 22, the fixation lamp 23, the oblique observation camera 24, and the front observation camera 25 are merely examples, and are not limited to these.

The light projection optical system 21 may be composed of a laser light source, a projection lens, a mirror, etc., and a known configuration as the light projection optical system of a laser flare meter can be applied. The light reception optical system 22 may be composed of an objective lens, a mirror, a light-receiving element, etc., and the fixation lamp 23 may be composed of an LED, a lens, etc. Like the light projection optical system 21, known configurations as the light reception optical system and fixation lamp of a laser flare meter can be applied.

The oblique observation camera 24 is a camera for observing the subject eye E from the optical axis direction of the light reception optical system 22. In the present embodiment, the oblique observation camera 24 is disposed to be in a state in which the camera optical axis is shifted 55° to the right from the central axis C of the optical head 2. The front observation camera 25 is a camera for observing the subject eye E approximately from the front direction. In the present embodiment, the front observation camera 25 is disposed to be in a state in which the camera optical axis is shifted 5° to the right from the central axis C of the optical head 2. Known configurations as imaging devices can be applied to the oblique observation camera 24 and the front observation camera 25. The oblique observation camera 24 and the front observation camera 25 may be used when performing the alignment of the optical head 2 and the setting of the measurement site of the subject eye.

The optical head 2 may be attached to the upper portion of the horizontal drive unit 3. The horizontal drive unit 3 is for driving the optical head 2 in the horizontal direction on the xz plane, and a known biaxial stage unit using two motors, for example, can be applied as the horizontal drive unit 3.

Figure 3:
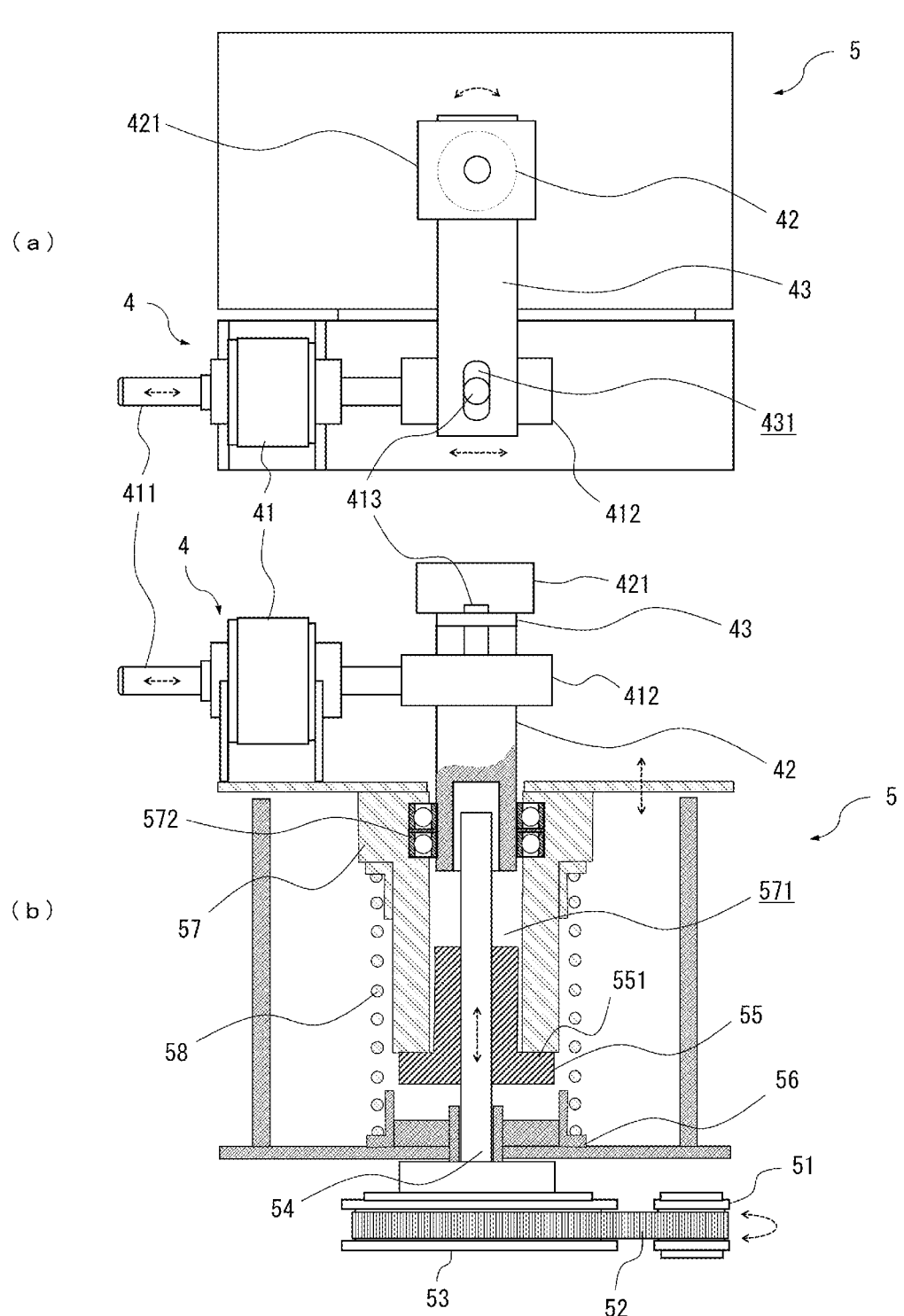
FIG. 3 is an explanatory diagram illustrating the structures of a rotational drive unit and a vertical drive unit of the ophthalmic device.

FIG. 3 is an explanatory diagram illustrating the structures of the rotational drive unit 4 and vertical drive unit 5 of the ophthalmic device 1, wherein (a) of FIG. 3 is a diagram in which the rotational drive unit 4 and the vertical drive unit 5 are viewed from above, and (b) of FIG. 3 is a diagram in which the rotational drive unit 4 and the vertical drive unit 5 are viewed from the side. In the structure of the present embodiment, as will be described below, the rotational drive unit 4 and the vertical drive unit 5 are integrated.

The rotational drive unit 4 includes a linear motion motor 41 that linearly moves a motor shaft 411 in the axial direction, a rotating shaft 42 having an upper portion provided with a connection portion 421 connected to the horizontal drive unit 3, and a rotating arm 43 having one end coupled to the motor shaft 411 of the linear motion motor 41 and the other end coupled to the rotating shaft 42. One end of the motor shaft 411 of the linear motion motor 41 is provided with a cuboid-shaped drive block 412, and a pin 413 having a cylindrical shape (perfectly circular shape in the cross section) is provided to stand vertically upward on the upper surface of the drive block 412.

The rotating arm 43 may be a plate-like member that is approximately rectangular in the plan view, and one end of the rotating arm 43 is formed with an oval-shaped insertion hole 431. The rotating arm 43 is coupled to the motor shaft 411 of the linear motion motor 41 by the pin 413 of the linear motion motor 41 being inserted in the insertion hole 431, and coupled to the rotating shaft 42 by fixing the other end side of the rotating arm 43 to the upper portion of the rotating shaft 42. With such a structure, when the motor shaft 411 of the linear motion motor 41 moves linearly in the axial direction, the pin 413 pushes the inner surface of the insertion hole 431 of the rotating arm 43 thereby to allow the end portion of the rotating arm 43 to move on the axis line of the motor shaft 411, resulting in the rotation of the rotating shaft 42 coupled to the other end of the rotating arm 43. As the rotating shaft 42 rotates, the horizontal drive unit 3 connected to the connection portion 421 of the rotating shaft 42 rotates, and the optical head 2 attached to the upper portion of the horizontal drive unit 3 can be driven to rotate.

The vertical drive unit 5 includes a motor 51, a motor pulley 53 connected to the motor 51 via a belt 52, a vertical feed screw 54 provided to stand at the center of the motor pulley 53, a nut 55 screwed on the vertical feed screw 54, a lower structure 56 having a central portion in which the vertical feed screw 54 is inserted, and an upper structure 57 having an accommodation space 571 in which the vertical feed screw 54, the nut 55, and the rotating shaft 42 of the rotational drive unit 4 are accommodated in the central portion of the accommodation space 571. The nut 55 screwed on the vertical feed screw 54 has a flange portion 551 that protrudes radially outward on its lower peripheral edge portion, and as the vertical feed screw 54 rotates by the rotation of the motor pulley 53, the nut 55 moves up and down along the vertical feed screw 54.

In the upper structure 57, the inner wall lower portion of the accommodation space 571 is in contact with the upper surface of the flange portion 551 of the nut 55, and when the nut 55 moves up and down, the upper structure 57 also moves up and down accordingly. In addition, the upper structure 57 is connected to the rotating shaft 42 of the rotational drive unit 4 via ball bearings 572 in the inner wall upper portion of the accommodation space 571, and when the upper structure 57 moves up and down, the rotating shaft 42 moves up and down together with the upper structure 57 while being in a rotatable state without being restrained by the upper structure 57. As the rotating shaft 42 moves up and down, the horizontal drive unit 3 connected to the connection portion 421 of the rotating shaft 42 moves up and down, and the optical head 2 attached to the upper portion of the horizontal drive unit 3 can be vertically driven. In this operation, the rotating shaft 42 serves as a component of the rotational drive unit 4 to rotationally drive the optical head 2 and also serves as a component of the vertical drive unit 5 to vertically drive the optical head 2. Sets of shafts and shaft bearings may be provided separately in parallel between the upper structure 57 and the lower structure 56 to prevent the upper structure 57 from rotating with respect to the lower structure 56 when moving up and down by the nut 55.

In the present embodiment, the vertical drive unit 5 includes a spring 58 as an elastic member between the lower structure 56 and the upper structure 57 for alleviating the load due to the rotational drive unit 4, the horizontal drive unit 3, and the optical head 2. The spring 58 is disposed between the lower structure 56 and the upper structure 57 so that the vertical feed screw 54, the nut 55, and the accommodation space 571 of the upper structure 57 are arranged inside the spring 58. The provision of an elastic member such as the spring 58 between the lower structure 56 and the upper structure 57 can alleviate the load due to the rotational drive unit 4, the horizontal drive unit 3, and the optical head 2, which are installed on the upper structure 57, and can thus reduce the burden on the lower structure 56, the vertical feed screw 54, the nut 55, etc., and it is therefore possible to prevent an increase in the sizes of components constituting the vertical drive unit 5.

As described above, in the present embodiment, the turning drive unit composed of the horizontal drive unit 3 and the rotational drive unit 4 is disposed on the vertical drive unit 5. By disposing each drive unit in this manner, the load applied to the turning drive unit (horizontal drive unit 3 and rotational drive unit 4) can be reduced, and it is therefore possible to avoid an increase in the sizes of components constituting the turning drive unit (horizontal drive unit 3 and rotational drive unit 4).

In particular, by setting the order of arranging the horizontal drive unit 3 and rotational drive unit 4 arranged on the vertical drive unit 5 so that the horizontal drive unit 3 is disposed on the rotational drive unit 4, the rotational drive unit 4 is disposed between the horizontal drive unit 3 and the vertical drive unit 5; therefore, the load applied to the rotational drive unit 4 can be reduced, and it is possible to avoid complicating the angle correction of an observation axis by the horizontal drive unit 3 while avoiding an increase in the sizes of components constituting the rotational drive unit 4. Specifically, if the rotational drive unit 4 is disposed on the horizontal drive unit 3, for example, the rotation of the rotational drive unit 4 will change the angular relationship between the optical axis of each optical system provided on the optical head 2 (the optical axis of the light projection optical system 21, light reception optical system 22, fixation lamp 23, oblique observation camera 24, or front observation camera 25) and the movement direction of the horizontal drive unit 3. (The optical axes of the optical systems are fixed on the base 26 of the optical head 2 in one housing in a state of maintaining their relationships with each other, so their respective angles do not change, but the angle formed between the movement direction of the horizontal drive unit 3 and the optical axis of each optical system changes by the amount of rotation of the rotational drive unit 4.)

For example, assuming that the front observation camera 25 on the optical head 2 is used to image a subject H almost from the front, when the turning angle is 0° with the rotational drive unit 4 at the top, the front observation camera 25 captures an image of the subject H from the front upon movement of the horizontal drive unit 3, and the front, back, right, and left move straight vertically and horizontally with respect to the image. When the angle is changed, for example, when the rotational drive unit 4 rotates the optical head 2 with a rotation angle of 45°, the movement of the horizontal drive unit 3 causes the front observation camera 25 to move vertically and horizontally with respect to the subject H in a state of obliquely imaging the subject H, and the front observation camera 25 therefore moves in a direction deviated by 45° from the observation direction of the camera. In order to correct this, the correction may be performed so that the horizontal drive unit 3 is moved in the observation direction of the camera when it is operated, but if the number of set rotation angles by the rotational drive unit 4 is large, it will be necessary to calculate and control the amount of correction every time the set angle is changed, which may be complicated.

On the other hand, when the rotational drive unit 4 is located below the horizontal drive unit 3, the angular relationship between the observation direction of the front observation camera 25 (optical head 2) and the movement direction of the horizontal drive unit 3 is always constant, and therefore regardless of the angle at which the rotation of the optical head 2 by the rotational drive unit 4 is set, the horizontal drive unit 3 will necessarily move straight vertically and horizontally with respect to the image captured by the front observation camera 25. In the ophthalmic device 1 according to the present embodiment, the fixation lamp 23 is also fixed to the optical head 2. As a result, the eyeball of the subject H also moves in accordance with the rotation of the optical head 2, and the subject H will constantly direct the subject eye E in the direction of the front observation camera 25. Thus, by disposing the rotational drive unit 4 below the horizontal drive unit 3, the horizontal drive unit 3 can be constantly controlled in the same xz directions to perform the alignment of the optical head 2 regardless of the angle of rotation of the optical head 2 by the rotational drive unit 4, and it is therefore possible to avoid complicating the angle correction of the observation axis by the horizontal drive unit 3.

Figure 4:
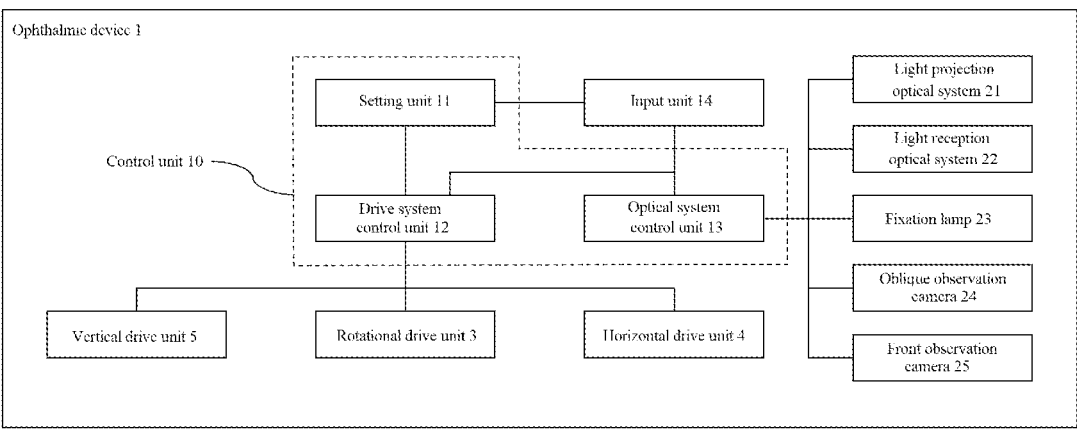
FIG. 4 is a block diagram illustrating the internal configuration of the ophthalmic device.

FIG. 4 is a block diagram illustrating the internal configuration of the ophthalmic device 1 according to the present embodiment. The ophthalmic device 1 has a setting unit 11 that sets the turning angle of the optical head 2, a drive system control unit 12 that controls the horizontal drive unit 3, the rotational drive unit 4, and the vertical drive unit 5, an optical system control unit 13 that controls the light projection optical system 21, the light reception optical system 22, the fixation lamp 23, the oblique observation camera 24, and the front observation camera 25, and an input unit 14 that includes a set of buttons, a touch panel, and/or a joystick for receiving the operation input and direction instruction input made by a user. The input unit 14 can input various information items from such a set of buttons, a touch panel, and/or a joystick. Buses are provided between the units to transmit control signals or data signals.

The drive system control unit 12 controls the turning drive unit, which is composed of the horizontal drive unit 3 and the rotational drive unit 4, so as to turn the optical head 2 in accordance with the turning angle set by the setting unit 11. In addition, the drive system control unit 12 controls the horizontal drive unit 3, the rotational drive unit 4, and the vertical drive unit 5 to perform the alignment of the optical head 2 so that appropriate observation is performed to match the subject eye E of the subject. The alignment of the optical head 2 by the drive system control unit 12 may be performed automatically by a program or the like that is preliminarily set (auto-alignment) or may also be performed manually by the input operation of an operator using a touch panel, a joystick, or the like of the input unit 14.

The optical system control unit 13 performs not only the light amount adjustment for light sources included in the light projection optical system 21 and the fixation lamp 23 and the focus control for the light projection optical system 21, the light reception optical system 22, the oblique observation camera 24, and the front observation camera 25 but also the generation and processing of various images based on the images acquired by the light reception optical system 22, the oblique observation camera 24, and the front observation camera 25, the calculation of a protein concentration in the anterior chamber of the subject eye E (flare value) based on the acquired images, etc.

Figure 5:
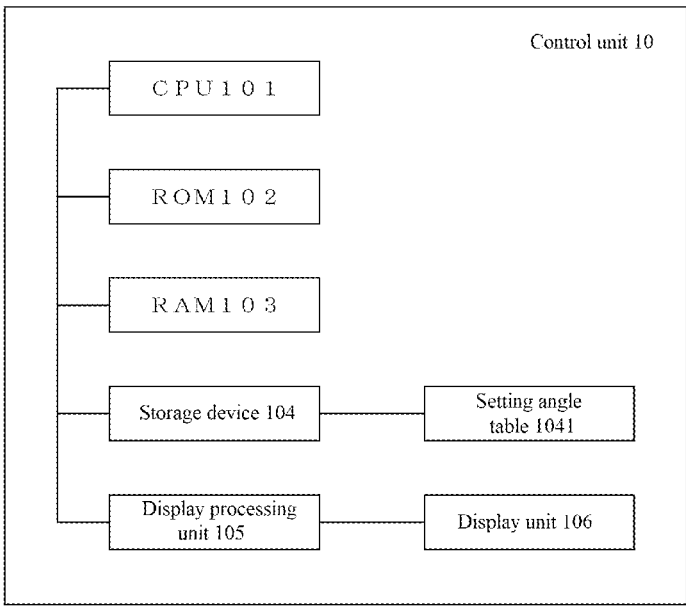
FIG. 5 is block diagram illustrating the configuration of a control unit of the ophthalmic device.

The setting unit 11, the drive system control unit 12, and the optical system control unit 13 can be implemented as one control unit 10. FIG. 5 is a block diagram illustrating the configuration of the control unit 10 of the ophthalmic device 1. The control unit 10 includes a CPU 101, a ROM 102, a RAM 103, a storage device 104, a display processing unit 105, and a display unit 106. Buses are provided between the units to transmit control signals or data signals. When the ophthalmic device 1 is powered on, the CPU 101 loads various programs stored in the ROM 102 or the storage device 104 into the RAM 103 and executes the programs. The storage device 104 may be, for example, a non-volatile storage device such as a flash memory, an SSD, a magnetic storage device (e.g., an HDD or the like), or an optical disk or may also be a volatile storage device such as a RAM. The storage device 104 stores programs which the CPU 101 executes and data which the CPU 101 refers to. The storage device 104 also stores a setting angle table 1041, which will be described below. The display processing unit 105 displays the data for display, which is provided from the CPU 101, on the display unit 106. As the display unit 106, for example, a liquid crystal display can be used.

The ophthalmic device 1 in the present embodiment is configured so that the optical head 2 can be turned in accordance with four predetermined turning angles (0 degrees, 5 degrees, 10 degrees, and 15 degrees). The storage device 104 stores a setting angle table 1041 as illustrated in Table 1, and when the operator selects any one of angles 1 to 4 using the input unit 14, the setting unit 11 selects one setting angle from the setting angle table 1041 in accordance with the input result from the input unit 14 and sets the one setting angle as the turning angle of the optical head 2. The turning angle of the optical head 2 is an angle with respect to the central axis C (i.e., the z-axis) of the optical head 2 as a reference (0 degrees). In the present embodiment, four angles are predetermined in increments of 5°, but the present invention is not limited to this, and the number of angles and the interval between them which should be predetermined can be set in accordance with the device configuration and the like.

TABLE 1

|  | Angle 1 | Angle 2 | Angle 3 | Angle 4 |
|---|---|---|---|---|
| Turning angle | 0° | 5° | 10° | 15° |

Rather than displaying the angles 1 to 4 for a target to be selected by the operator using the input unit 14, for example, the operator may be allowed to directly select 0°, 5°, 10°, or 15° or select one from four options: the height of the subject's nose is "normal," "slightly high," "high", or "very high" (for example, when the subject's nose is "very high," the setting angle table 1041 may be stored with a turning angle of "15°").

Figure 6:
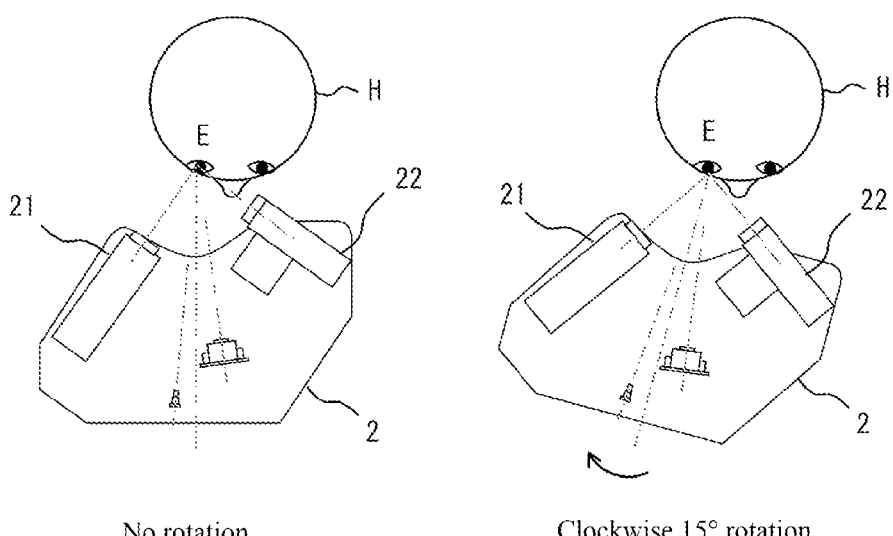
FIG. 6 is a set of explanatory diagrams illustrating how the optical head of the ophthalmic device turns.
Figure 6:
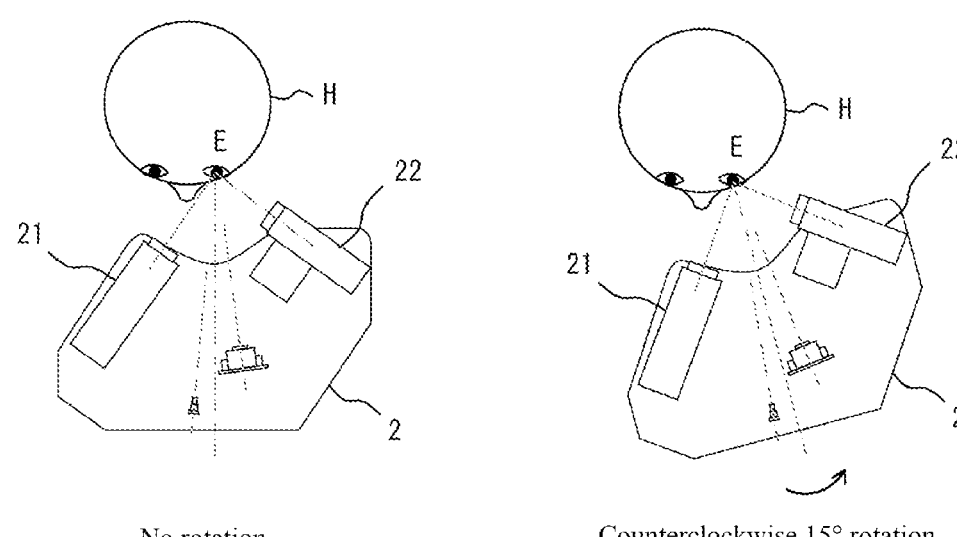

The turning direction of the optical head 2 may be determined in accordance with the configuration of the ophthalmic device and/or whether the subject eye is the right eye or the left eye. In order to prevent the ophthalmic device 1 from coming into contact with the face of the subject H, it is preferred to turn the optical head 2 in a direction in which a portion of the optical head 2 suspected to come into contact with the subject H moves away from the face of the subject. In many cases, the portion of the optical head 2 suspected to come into contact with the subject H may be a portion of the optical head 2 positioned closest to the face of the subject H. As illustrated in FIGS. 6(*a*) and 6(*b*), in the ophthalmic device 1 according to the present embodiment, when the subject eye E is the right eye, the light reception optical system 22 of the optical head 2 is positioned closest to the face of the subject H (in particular, the nose protruding toward the ophthalmic device 1), and the optical head 2 is therefore rotated in a direction of moving away from the nose, that is, rotated clockwise when the ophthalmic device 1 and the subject H are viewed from above (see FIG. 6(*a*)). On the other hand, when the subject eye E is the left eye, the light projection optical system 21 is positioned close to the face of the subject H (in particular, the nose protruding toward the ophthalmic device 1), and the optical head 2 is therefore rotated in a direction of moving away from the nose, that is, rotated counterclockwise when the ophthalmic device 1 and the subject H are viewed from above (see FIG. 6(*b*)). That is, in the present embodiment, the direction in which the portion of the optical head 2 positioned closest to the face of the subject H moves away from the face of the subject H differs between when the subject eye E is the right eye and when the subject eye E is the left eye.

The turning direction of the optical head 2 may be set in the same manner as for the turning angle so that when the operator selects whether the subject eye E is the right eye or the left eye using the input unit 14, the setting unit 11 sets either the clockwise direction or the counterclockwise direction as the turning direction of the optical head 2 in accordance with the input result from the input unit 14.

In the present embodiment, the setting unit 11 sets the turning angle and turning direction of the optical head 2 in accordance with the input result from the input unit 14 by the operator, but the ophthalmic device 1 may be provided with a range sensor (not illustrated) or the like, for example, and the ophthalmic device 1 may be configured to detect/estimate the positional relationship between the subject H and the device and the features and shape of the face of the subject H, and the setting unit 11 may automatically set appropriate turning angle and/or turning direction of the optical head 2.

The description will then be directed to a flow for measuring the flare value of the subject eye E of the subject H using the above-described ophthalmic device 1. First, the subject H rests his/her chin on a chin support (not illustrated) provided for the ophthalmic device 1.

Subsequently, the operator (examiner) uses the input unit 14 to select (input) whether the subject eye E is the right eye or the left eye. In addition, the operator observes the face (such as nose) of the subject H to determine which of the angles 1 to 4 the turning angle of the optical head 2 should be, and uses the input unit 14 to select (input) any one of the angles 1 to 4. For example, the operator selects any one of the angles 1 to 4 so that the higher the nose of the subject H, the larger the turning angle of the optical head 2.

After the setting unit 11 sets the turning direction and turning angle of the optical head 2 in accordance with the input result (operator's selection result) from the input unit 14, the drive system control unit 12 controls the turning drive unit (horizontal drive unit 3 and rotational drive unit 4) to turn the optical head 2. For example, assuming that the subject eye E is the right eye and the nose of the subject H is high, the input result from the input unit 14 is "right eye" and "angle 3," so the setting unit 11 sets the turning direction of the optical head 2 clockwise and the turning angle to 10°. In response to this, the drive system control unit 12 controls the turning drive unit (horizontal drive unit 3 and rotational drive unit 4) to rotate the optical head 2 clockwise by 10°.

After that, the image data of the subject eye E acquired by the oblique observation camera 24 and the front observation camera 25 is displayed on the display unit 106 by the display processing unit 105, and the operator therefore performs the alignment of the optical head 2 so that the measurement window comes to the measurement site of the subject eye E. This alignment may be performed manually using a joystick or the like of the input unit 14 or may also be performed automatically using an auto-alignment function.

After the alignment is completed, the measurement site of the subject eye E is irradiated with laser light from the light projection optical system 21 to scan the measurement window, and the scattered light from the subject eye E is received by the light reception optical system 22 to measure the flare value.

According to the ophthalmic device 1 as described above, the turning drive unit turns the optical head 2 in the horizontal direction while maintaining the positional relationships between the light projection optical system 21, the light reception optical system 22, and the fixation lamp 23, so that the subject eye E of the subject H moves to follow the light from the fixation lamp 23, and the optical head 2 can therefore be moved away from the face of the subject H in a state in which the light projection optical system 21 and the light reception optical system 22 are still capturing the measurement site of the subject eye E. This can result in an increased distance between the optical head 2 and the face of the subject H, thereby avoiding contact between the ophthalmic device 1 and the face of the subject H without imposing a burden on the body of the subject H. Moreover, even in a limited space such as in a housing of the ophthalmic device 1, for example, the structure for turning the optical head 2 can be achieved by appropriately arranging the rotational drive unit 4 and the horizontal drive unit 3. Furthermore, the setting unit 11 can set a turning angle that matches the features of the face of the subject H, and the drive system control unit 12 can control the turning drive unit (horizontal drive unit 3 and rotational drive unit 4) to turn in accordance with the turning angle; therefore, it is possible to achieve the turning of the optical head 2 matching the features of the face of the subject H.

Modified Example

In the above embodiment, the setting unit 11 is configured to set one angle selected from a plurality of predetermined angles as the turning angle, but the setting unit 11 may set the turning angle so that the optical head 2 turns by a predetermined unit angle. For example, the touch panel of the input unit 14 may be provided with a "+" button, a "0" button, and a "−" button, and the turning angle may be set so that when the operator presses the "+" button, the optical head 2 rotates clockwise by 5 degrees while when the operator presses the "−" button, the optical head 2 turns counterclockwise by 5 degrees. Additionally or alternatively, the optical head 2 may be configured to return to the reference position (0°) when the operator presses the "0" button. Any angle can be adopted as the unit angle by which the optical head 2 turns each time the "+" button or the "−" button is pressed.

While the ophthalmic device according to the present invention has been described above with reference to the drawings, the present invention is not limited to the above embodiments, and various modifications can be carried out. For example, in the above embodiment, as illustrated in FIG. 6, the optical head 2 is turned clockwise when the subject eye E is the right eye, and the optical head 2 is turned counterclockwise when the subject eye E is the left eye, but the present invention is not limited to this, and the right or left direction in which the optical head 2 moves away from the face of the subject H may be reversed depending on the configuration of the device. Moreover, the turning direction of the optical head 2 may be the same regardless of whether the subject eye E is the right eye or the left eye and only the turning amount (turning angle) may be different.

Furthermore, the ophthalmic device is not limited to a laser flare meter, and may be a slit lamp, a fundus camera, a scanning laser ophthalmoscope (in particular, one with a wide angle), or the like. The present invention is particularly effective when the ophthalmic device is a laser flare meter because the laser flare meter has characteristics of emitting the laser obliquely and receiving the scattered light from the opposite oblique direction and optical components are arranged in a portion closer to the subject eye.

DESCRIPTION OF REFERENCE NUMERALS

1 Ophthalmic device
10 Control unit

11 Setting unit
12 Drive system control unit
13 Optical system control unit
14 Input unit
2 Optical head
21 Light projection optical system
22 Light reception optical system
23 Fixation light
24 Oblique observation camera
25 Front observation camera
26 Base
3 Horizontal drive unit
4 Rotational drive unit
41 Linear motion motor
42 Rotating shaft
43 Rotating arm
5 Vertical drive unit
51 Motor
52 Belt
53 Motor pulley
54 Vertical feed screw
55 Nut
56 Lower structure
57 Upper structure
58 Spring (elastic member)
H Subject
E Subject eye

The invention claimed is:

1. An ophthalmic device comprising:
an optical head including a light projection optical system that projects light onto a subject eye, a light reception optical system that receives light from the subject eye, and a fixation lamp for guiding a line-of-sight direction of the subject eye during measurement of the subject eye; and
a turning drive that turns the optical head in a horizontal direction while maintaining positional relationships between the light projection optical system, the light reception optical system, and the fixation lamp,
the turning drive including a rotational drive that rotates the optical head in the horizontal direction and a horizontal drive that moves the optical head in the horizontal direction,
wherein the fixation lamp is fixed to the optical head together with the light projection optical system and the light reception optical system.

2. The ophthalmic device according to claim 1, wherein the turning drive is controlled so that the optical head turns in a direction in which a portion of the optical head suspected to come into contact with a subject moves away from the face of the subject.

3. The ophthalmic device according to claim 2, wherein the direction in which the portion of the optical head moves away from the face of the subject differs between when the subject eye is the right eye and when the subject eye is the left eye.

4. The ophthalmic device according to claim 1, further comprising
a controller that sets a turning angle of the optical head and
controls the turning drive so as to turn the optical head in accordance with the turning angle.

5. The ophthalmic device according to claim 4, wherein the controller sets one angle selected from a plurality of predetermined angles as the turning angle.

6. The ophthalmic device according to claim 4, wherein the controller sets the turning angle so that the optical head turns by a predetermined unit angle.

7. The ophthalmic device according claim 1, further comprising a vertical drive that moves the optical head in a vertical direction.

8. The ophthalmic device according to claim 7, wherein the turning drive is disposed on the vertical drive.

9. The ophthalmic device according to claim 8, wherein the horizontal drive is disposed on the rotational drive.

10. The ophthalmic device according to claim 8, wherein the vertical drive includes an elastic member for alleviating a load due to the rotational drive, the horizontal drive, and the optical head.

11. The ophthalmic device according claim 1, wherein the optical head further includes a camera that images the subject eye.

12. The ophthalmic device according to claim 11, wherein the camera includes a front observation camera and an oblique observation camera.

13. The ophthalmic device according to claim 1, wherein the light projection optical system projects projection light onto a measurement site of the subject eye obliquely with respect to an eyeball optical axis of the subject eye, and the light reception optical system receives scattered light of the projection light that is scattered at the measurement site of the subject eye.

* * * * *